United States Patent [19]

Briner

[11] Patent Number: 5,151,550

[45] Date of Patent: Sep. 29, 1992

[54] CYCLOPENTANE DERIVATIVES

[75] Inventor: Paul H. Briner, Canterbury, England

[73] Assignee: Shell Research Limited, United Kingdom

[21] Appl. No.: 746,874

[22] Filed: Aug. 19, 1991

[30] Foreign Application Priority Data

Sep. 3, 1990 [GB] United Kingdom ................. 9019191

[51] Int. Cl.$^5$ ............................................ C07C 62/04
[52] U.S. Cl. ................................................... 562/468
[58] Field of Search ........................................ 562/468

[56] References Cited

U.S. PATENT DOCUMENTS 4,400,534 8/1983 Terada et al. ....................... 562/468

FOREIGN PATENT DOCUMENTS 0267778 5/1988 European Pat. Off. .
2180236 3/1987 United Kingdom .

Primary Examiner—Marianne M. Cintins
Assistant Examiner—John Peabody

[57] ABSTRACT

The invention provides a process for the preparation of cyclopentanediol derivatives of the general formula

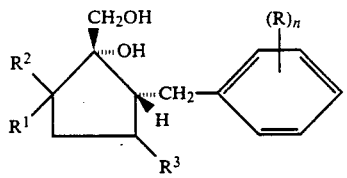 (I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; and $R^1$, $R^2$ and $R^3$ independently represent a hydrogen atom or an alkyl group; which comprises reacting a cyclopentanol derivative of the general formula

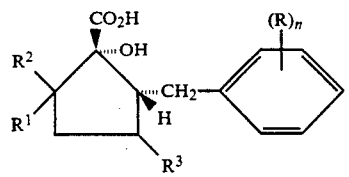 (II)

with a reducing agent. The invention also provides the cyclopentanol derivative intermediates of formula II per se and a process for their preparation. Compounds of formulae I and II are useful as intermediates in the preparation of certain fungicidally active cyclopentane derivatives.

5 Claims, No Drawings

CYCLOPENTANE DERIVATIVES

This invention relates to a process for the preparation of cyclopentanediol derivatives via cyclopentanol derivative intermediates, the cyclopentanol derivatives per se and a process for their preparation. The cyclopentanediol and cyclopentanol derivatives are useful as intermediates in the preparation of certain fungicidally active cyclopentane derivatives.

According to the present invention there is provided a process for the preparation of a compound of the general formula

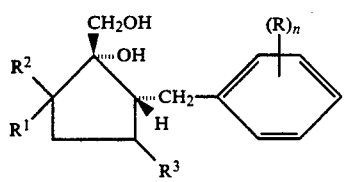

(I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; and $R^1$, $R^2$ and $R^3$ independently represent a hydrogen atom or an alkyl group; which comprises reacting a compound of the general formula

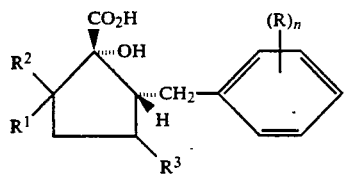

(II)

in which n, R, $R^1$, $R^2$ and $R^3$ are as defined above, with a reducing agent.

It is preferred that the reducing agent is a complex metal hydride, such as lithium aluminium hydride, "REDAL" (Trade Mark: sodium bis(2-methoxyethoxy)aluminium hydride in toluene) or sodium borohydride in the presence of aluminium chloride.

The process is conveniently carried out in the presence of a solvent. Suitable solvents include ethers, such as diethyl ether and diglyme, and hydrocarbons, such as toluene.

Preferably, the reaction is carried out at a temperature from 0° C. to the reflux temperature of the solvent depending on the nature of the reducing agent selected.

It is advisable to destroy any excess reducing agent remaining at the end of the reduction process to prevent further reaction. If a complex metal hydride, such as lithium aluminium hydride, is used as reducing agent, any excess may be destroyed by the addition of water and sodium hydroxide or ammonium chloride to the reaction mixture.

According to the present invention there is provided a compound of the general formula

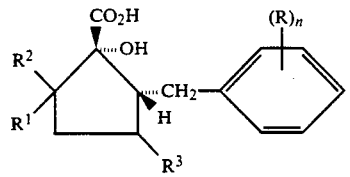

(II)

in which n, R, $R^1$, $R^2$ and $R^3$ are as previously defined.

The present invention further provides a process for the preparation of a compound of formula II as defined above which comprises heating a compound of the general formula

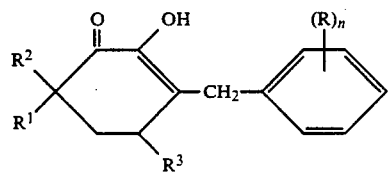

(III)

or the general formula

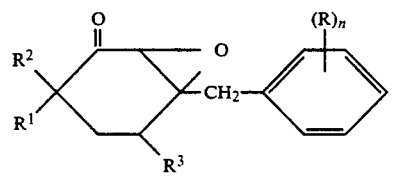

(IV)

in which n, R, $R^1$, $R^2$ and $R^3$ are as defined above, with an alkali metal hydroxide, especially sodium or potassium hydroxide, in the presence of a polar solvent.

Preferably, the polar solvent is a high boiling oligoether, such as 2-(2-methoxyethoxy)ethanol, or an alcohol, preferably a $C_{1-6}$ and especially a $C_{4-6}$ tertiary alcohol. The reaction is conveniently carried out at a temperature from 130° C. to the reflux temperature of the solvent, preferably from 135° to 155° C.

Compounds of formula III may be conveniently prepared by reacting a compound of formula IV in which n, R, $R^1$, $R^2$ and $R^3$ are as defined above, with a compound of the general formula $$MOR^5 \qquad (V)$$

in which $R^5$ represents a hydrogen atom or an alkyl, preferably a $C_{1-6}$ tertiary alkyl and especially a $C_{4-6}$ tertiary alkyl, or cycloalkyl, preferably a $C_{3-6}$ cycloalkyl, group and M represents an alkali metal, preferably a sodium or potassium, atom in the presence of a polar solvent. The compounds of formula III and a process for their preparation form the subject of copending patent application T 690.

Compounds of formula IV may be conveniently prepared by reacting a compound of formula

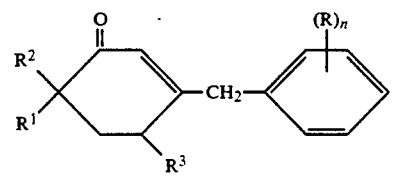

(VI)

in which n, R, $R^1$, $R^2$ and $R^3$ are as defined above, with hydrogen peroxide in the presence of a base, preferably an inorganic base such as sodium hydroxide, potassium hydroxide or a quaternary ammonium hydroxide. The compounds of formula IV and a process for their preparation form the subject of copending patent application T 690.

Compounds of formula VI may be conveniently prepared by reacting a compound of formula

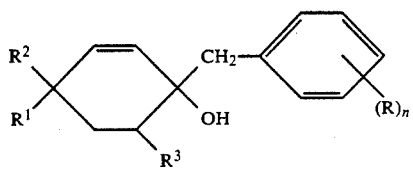
(VII)

in which n, R, $R^1$, $R^2$ and $R^3$ are as defined above, with an oxidising agent, preferably a chromium (VI) salt such as an alkali metal dichromate, particularly sodium dichromate or potassium dichromate. The compounds of formula VI and a process for their preparation form the subject of copending patent application T 690.

Compounds of formula VII may be conveniently prepared by reacting a compound of formula

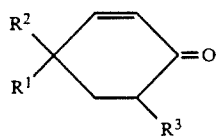
(VIII)

in which $R^1$, $R^2$ and $R^3$ are as defined above, with a compound of the general formula

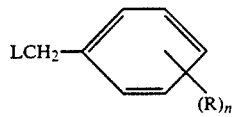
(IX)

in which R and n are as defined above and L represents an organometallic group, such as lithium or the group —MgHal where Hal represents a chlorine or bromine atom. The compounds of formula VII and a process for their preparation form the subject of copending patent application T 689.

Compounds of formula V, VIII and IX are known compounds or can be prepared by processes analogous to known processes.

When any of the foregoing substituents represents or contains an alkyl substituent group, this may be linear or branched and may contain up to 12, preferably up to 6, and especially up to 4 carbon atoms. A cycloalkyl substituent group may contain 3 to 8, preferably 3 to 6, carbon atoms.

It is preferred that $R^1$, $R^2$ and $R^3$ independently represent a hydrogen atom or a $C_{1-4}$ alkyl, particularly a methyl group.

Preferably, R represents a halogen, especially a chlorine atom.

A particularly preferred sub-group of compounds of formulae I and II is that in which n is 1, R represents a chlorine atom, preferably substituted at the 4- position of the phenyl ring, $R^1$ and $R^2$ both represent a hydrogen atom or both represent a methyl group and $R^3$ represents a hydrogen atom or methyl group.

The compounds of formula I are useful as intermediates in the preparation of fungicidally active cyclopentane derivatives of the general formula

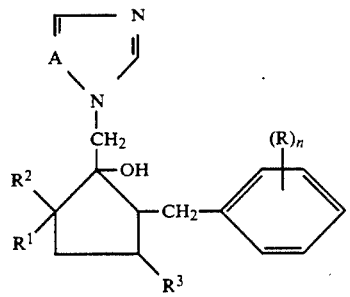
(X)

in which n, R, $R^1$, $R^2$ and $R^3$ are as defined above and A represents a nitrogen atom or a CH group. Certain compounds of formula X are the subject of co-pending patent applications GB-A1-2180236 and EP-A2-0267778. The compounds disclosed in EP-A2-0267778 and GB-A1-2180236 exist in two stereoisomeric forms which have the following structures:

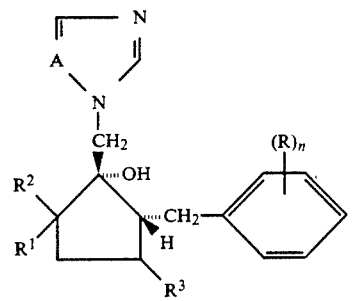
(XA)

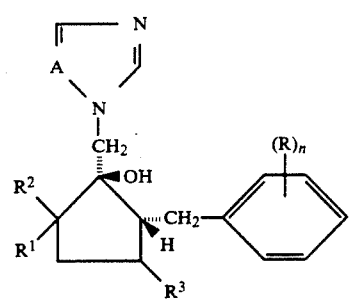
(XB)

The letters A and B will be used hereinafter to denote compounds having the same stereochemical configuration as isomers A and B above.

Isomers A and B can be separated by, for instance, chromatography and exhibit different fungicidal activity. Generally, isomers of formula XA exhibit greater fungicidal activity than isomers of formula XB. The process used to synthesise compounds of formula XA from compounds of formula I is set out in the following reaction scheme:

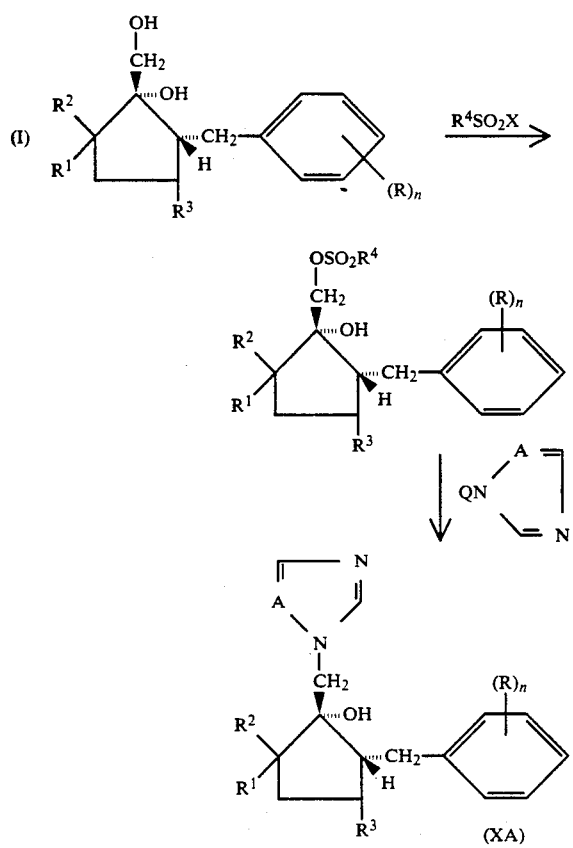

In the above reaction scheme, n, R, $R^1$, $R^2$, $R^3$, M and A are as previously defined, $R^4$ represents an optionally substituted alkyl or aryl group, preferably a $C_{1-4}$alkyl or a phenyl group each optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups, X represents a halogen, preferably a chlorine or bromine, atom and Q represents a hydrogen or alkali metal, preferably sodium or potassium, atom. The compounds of formula I per se and the intermediate compounds and process steps in the above reaction scheme are the subject of copending European patent application no 89202159.3 and copending British patent application no. 8820607.3.

The invention is further illustrated by the following examples.

EXAMPLE 1

Preparation of 1-(4-chlorobenzyl)-2-carboxyl-2-hydroxy-3,3-dimethylcyclopentane (Formula II: n=1, R=4-Cl, $R^3$=H)

(a) Preparation of 1-(4-chlorobenzyl)-4,4-dimethylcyclohex-2-en-1-ol

A solution of 4-chlorobenzyl chloride (266 g, 1.65 mol) in diethyl ether (200 ml) was added slowly to a stirred mixture of magnesium (42 g, 1.73 mol) in diethyl ether (700 ml) to maintain the mixture at reflux. The mixture was warmed for a further 20 minutes after addition was complete. A solution of 4,4-dimethylcyclohex-2-en-1-one (226 g, 1.82 mol) in diethyl ether (60 ml) was then added dropwise over a period of 30 minutes so as to maintain the mixture at reflux and the mixture stirred overnight. The mixture was then quenched with water (250 ml) and hydrochloric acid (5M, 500 ml), extracted with diethyl ether (3×400 ml), backwashed once with sodium bicarbonate solution (5% w/v) and once with water and then dried with anhydrous magnesium sulphate. The solvent was then flashed off to give 369 g 1-(4-chlorobenzyl)-4,4-dimethylcyclohex-2-en-1-ol as an oil.

NMR (in $CDCl_3$ solvent, tetramethylsilane as reference) Characteristic peaks at:

$\delta$(ppm) 0.90, 0.99 (3H, singlet), 2.78 (2H, singlet), 5.40 (1H, doublet, J=11 Hz), 5.50 (1H, doublet, J=11 Hz), 7.17 (2H, doublet, J=8 Hz), 7.26 (2H, doublet, J=8 Hz)

(b) Preparation of 1-(4-chlorobenzyl)-4,4-dimethylcyclohex-1-en-3-one

A solution of the 1-(4-chlorobenzyl)-4,4-dimethylcyclohex-2-en-1-ol (368 g, 1.47 mol) obtained in (a) in 40/60 petroleum (40 ml) was added in a steady stream to a solution of sodium dichromate (217 g, 0.74 mol) in dilute sulphuric acid (250 g, 2.6 mol 98% sulphuric acid in 1.5 liters of water). The reaction mixture was then held at a temperature between 10° and 30° C. and stirred for 40 minutes. Water (500 ml) and diethyl ether (700 ml) were added and the aqueous layer extracted twice with diethyl ether (2×700 ml). The organic phases were then combined and backwashed with saturated sodium bicarbonate solution (1×500 ml) and water (1×500 ml). The solvent was then flashed off to give 349 g crude 1-(4-chlorobenzyl)-4,4-dimethylcyclohex-1-en-3-one as a beige coloured granular solid. Trituration in petrol gave a pure sample of the desired product, m.pt. 87°-90° C.

(c) Preparation of 1-(4-chlorobenzyl)-1,2-epoxy-4,4-dimethylcyclohexan-3-one 1726 g (6.945 mol) crude 1-(4-chlorobenzyl)-4,4-dimethylcyclohex-1-en-3-one obtained as described in (b) above and ethanol (8630 ml) were charged into a 20 liter reactor and warmed to 40° C. to give a clear pale orange solution. The reaction mixture was then cooled to 18° C. and 20% (w/v) sodium hydroxide (650 ml) was added slowly with cooling (ice/water) to maintain this temperature. Keeping the reaction mixture at a temperature between 11° and 20° C., 30% (w/v) aqueous hydrogen peroxide (794 ml, 7 mol) was added over a period of 1 hour and the mixture was then stirred overnight. Water (16 liters) was then added with ice cooling and the reaction mixture stirred for 15 minutes. Centrifugation followed by washing with water (4×2½ liters) yielded an off-white solid which was then air dried to give 1634 g 1-(4-chlorobenzyl)-1,2-epoxy-4,4-dimethylcyclohexan-3-one, m.pt. 69°-70° C.

(d) Preparation of 1-(4-chlorobenzyl)-2-carboxyl-2-hydroxy-3,3-dimethylcyclopentane 1000 g (3.78 mol) Crude 1-(4-chlorobenzyl)-1,2-epoxy-4,4-dimethylcyclohexan-3-one obtained in (c) above was dissolved in tert-butanol (4200 ml) at 40°-50° C. and the temperature raised at to 55° C. Solid potassium hydroxide (2×125 g portions) was added and the reaction mixture was then left for 1½ hours. 2-(2-Methoxyethoxy)ethanol (4200 ml) was then gradually added whilst the reaction mixture was heated to 150° C. for 6½ hours to remove the tert-butanol by short column distillation (4 liters recovered). The mixture was then cooled overnight and 4.5M hydrochloric acid (3.5 liters) was added with dry ice/acetone cooling to keep the reaction mixture at 20° C. The mixture was then stirred for 30 minutes, centrifuged and washed with water (4 liters). The solid residue was then taken into toluene, azeotropically dried, cooled overnight, centrifuged and washed with 60/80 petroluem (2 liters) to give 655 g 1-(4-chlorobenzyl)-2-carboxyl-2-hydroxy-3,3-dimethylcyclopentane as a white crystalline solid, m.pt. 157°-158° C.

EXAMPLE 2

Preparation of 1-(4-chlorobenzyl)-2-hydroxy-2-hydroxymethyl-3,3-dimethylcyclopentane (Formula I: n=1, R=4-Cl, , $R^3$=H)

A 35% solution of "REDAL" (Trade Mark: sodium bis(2-methoxyethoxy) aluminium hydride in toluene) (5 ml, 1.25 equivalents active hydrogen) was added to a suspension of 1-(4-chlorobenzyl)-2-carboxyl-2-hydroxy-3,3-dimethylcyclopentane (1 g) obtained in Example 1 above at 0°-5° C. The reaction mixture was then heated to 60°-70° C. overnight and worked up by backwashing with 5M hydrochloric acid. The mixture was then reextracted and the phases combined, washed twice with water and the solvent flashed off to give 0.8 g 1-(4-chlorobenzyl)-2-hydroxy-2-hydroxymethyl-3,3-dimethylcyclopentane as a solid, m.pt. 103°-104° C.

EXAMPLE 3

Preparation of 1-(4-chlorobenzyl)-2-carboxyl-2-hydroxy-3,3,5-trimethylcyclopentane (Formula II: n=1,R=4-Cl, $R^1=R^2=R^3=CH_3$)

(a) Preparation of 1-(4-chlorobenzyl)-4,4,6-trimethylcyclohex-2-en-1-ol

To a slurry of magnesium turnings (66 g, 2.73 g atoms) in diethyl ether (300 ml) was added a solution of 4-chlorobenzyl chloride (418 g, 2.6 moles) in diethyl ether (1500 ml) at such a rate as to maintain gentle reflux. After a further 30 minutes, a solution of 4,4,6-trimethylcyclohex-2-en-1-one (340 g, 2.46 moles) in diethyl ether (350 ml) was added, again maintaining a gentle reflux. After 1 hour the mixture was added into saturated aqueous ammonium chloride (4 liters) and the phases separated. The ether phase was back-washed with water (1 liter) and used directly in the next reaction. A small portion of 1-(4-chlorobenzyl)-4,4,6-trimethylcyclohex-2-en-1-ol was isolated for characterisation (gas chromatography analysis showed two isomers in approximately equal amounts).

NMR (in $CDCl_3$ solvent, tetramethylsilane as reference). Characteristics peak at:

δ(ppm) 0.75, 0.95, 1.00, 1.02, 1.05, 1.07, 1.09 (total 9H), 2.00 (1H,multiplet), 2.57, 2.79 (2H, AB, J=12 Hz), 2.69, 2.94 (2H, AB, J=12 Hz), 4.94 (1H, doublet, J=10 Hz), 5.34 (1H, doublet, J=10 Hz), 7.1–7.4 (4H).

(b) Preparation of 1-(4-chlorobenzyl)-4,4,6-trimethylcyclohex-1-en-3-one

A solution of sodium dichromate (281 g, 0.943 mol) in dilute sulphuric acid (428 g 98% sulphuric acid in 2.5 liters of water) was added to the ethereal solution of 1-(4-chlorobenzyl)-4,4,6-trimethylcyclohex-2-en-1-ol obtained in (a). The reaction mixture was then heated to 50–60° C. for 3–4 hours, cooled and quenched with water (2 liters) and diethyl ether (1 liter). The phases were separated and the organic phase was washed with 20% (w/v) sodium hydroxide (2×500 ml) to give a clear pale brown solution. Stripping off the solvent gave a mixture of crystalline solid and oily liquid which was then triturated in 60/80 petroleum (1 liter) at 0° C. and filtered to give 315 g 1-(4-chlorobenzyl)-4,4,6-trimethylcyclohex-1-en-3-one as a crystalline white solid, m.pt. 76°-77° C.

(c) Preparation of 1-(chlorobenzyl)-1,2-epoxy-4,4,6-trimethylcyclohexan-3-one

The 1-(chlorobenzyl)-4,4,6-trimethylcyclohexan-3-one (315 g, 1.2 mol) obtained in (b) above was added to methanol (1500 ml) and the mixture warmed to 40° C. to give a clear yellow solution. The solution was then cooled to 10° C. and aqueous sodium hydroxide (25 g in 112 ml water) was added over a period of 10 minutes. Whilst maintaining the temperature of the reaction mixture between 15° and 20° C., 30% (w/v) aqueous hydrogen peroxide (138 ml, 1.2 mol) was added over a period of 30 minutes and the mixture was then stirred overnight. A further 30 ml was then added and the mixture stirred for 2½ hours. The reaction mixture was then concentrated under reduced pressure and diluted with water (2 liters) and diethyl ether (1.5 liters). The aqueous layer was then extracted with diethyl ether (2×0.5 liters), dried and the solvent flashed off to give 1-(4-chlorobenzyl)-1,2-epoxy-4,4,6-trimethylcyclohexan-3-one as a crystalline white solid (271 g), m.pt. 58°-59° C.

(d) Preparation of 1-(4-chlorobenzyl)-2-carboxyl-2-hydroxy-3,3,5-trimethylcyclopentane Flake potassium hydroxide (30.4 g, 3 equivalents) was added to a solution of the 1-(4-chlorobenzyl)-1,2-epoxy-4,4,6-trimethylcyclohexan-3-one (43 g, 0.154 mol) obtained in (c) above in tert-butanol (200 ml) at 40°-50° C. and the mixture brought to reflux for 3 hours. A solvent switch to 2-(2-methoxyethoxy)ethanol (150 ml) was effected by distillation of tert-butanol through a short column whilst dosing the 2-(2-methoxyethoxy)ethanol. The temperature was gradually raised to 140°-150° C. and held at that temperature for 6 hours. The reaction mixture was then poured into ice-cold 2M hydrochloric acid (400 ml) and the solid filtered, washed with water and dissolved in refluxing toluene (150 ml) under a Dean-Stark separator. The mixture was then cooled, refiltered, washed with toluene then 40/60 petroluem and dried to give 34 g 1-(4-chlorobenzyl)-2-carboxyl-2-hydroxy-3,3-5-trimethylcyclopentane as a white solid, m.pt. 170°-171° C.

EXAMPLE 4

Preparation of 1-(4-chlorobenzyl)-2-hydroxy-2-hydroxymethyl-3,3,5-trimethylcyclopentane (Formula I: n=1, R=4-Cl, 34 g 1-(4-chlorobenzyl)-2-carboxyl-2-hydroxy-3,3,5-trimethylcyclopentane obtained in Example 3 above was added to a suspension of lithium aluminium hydride (17 g) in diethyl ether (200 ml) and the mixture refluxed overnight. The mixture was worked up with water (17 ml), 15% (w/v) sodium hydroxide (17 ml) and more water (51 ml) and the solvent flashed off to give 32 g 1-(4-chlorobenzyl)-2-hydroxy-2-hydroxymethyl-3,3,5-trimethylcyclopentane as a white solid, m.pt. 93°-94° C.

I claim:

1. A compound defined by the formula:

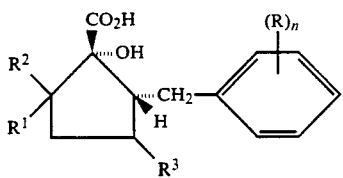

in which n represents an integer from 0 to 5;
each R represents a halogen atom, nitro, hydroxyl, alkyl, haloalkyl, alkoxy, haloalkoxy, amino, alkylamino, dialkylamino, carboxyl, alkanoyl, alkylthio, alkylamido, cycloalkyl or phenyl;
and $R^1$, $R^2$ and $R^3$ independently represent a hydrogen atom or an alkyl group.

2. A compound according to claim 1 wherein $R^1$, $R^2$ and $R^3$ independently represent a $C_{1-4}$ alkyl group.

3. A compound according to claim 1 wherein $R^1$, $R^2$ and $R^3$ independently represent a hydrogen atom or a methyl group.

4. A compound according to claim 1 wherein R represents a halogen atom.

5. A compound according to claim 1 wherein n is 1, R represents a chlorine atom, $R^1$ and $R^2$ both represent a hydrogen atom or both represent a methyl group, and $R^3$ represents a hydrogen atom or a methyl group.

* * * * *